United States Patent [19]

Popescu et al.

[11] Patent Number: 4,517,167
[45] Date of Patent: May 14, 1985

[54] CONTINUOUS REMOVAL OF ETHYLENE OXIDE FROM GASEOUS STREAMS

[75] Inventors: Miron Popescu, Trevose; Edward K. Gunsalus, Norristown, both of Pa.

[73] Assignee: Johnson & Johnson, New Brunswick, N.J.

[21] Appl. No.: 497,990

[22] Filed: May 25, 1983

[51] Int. Cl.³ .............................................. B01D 53/34
[52] U.S. Cl. ...................................................... 423/245
[58] Field of Search ................ 55/53; 422/34; 423/245

[56] References Cited

U.S. PATENT DOCUMENTS 4,112,054  9/1978  Feingold et al. ...................... 422/34
4,431,608  2/1984  Katagiri et al. ........................ 55/53

*Primary Examiner*—Ivars Cintins
*Attorney, Agent, or Firm*—Jason Lipow

[57] ABSTRACT

A system is provided for removing ethylene oxide from a gaseous stream without the need for large quantities of a liquid heat sink. A vessel is provided containing an aqueous acid solution and having a gas diffusion means submerged in the solution. The gaseous stream from which the ethylene oxide is to be removed is continuously diffused through the gas diffusion means and bubbles out of the acid solution while the inert essentially ethylene oxide free gas is continuously removed from above the solution.

9 Claims, 3 Drawing Figures

CONTINUOUS REMOVAL OF ETHYLENE OXIDE FROM GASEOUS STREAMS

BACKGROUND OF THE INVENTION

This invention relates to the continuous removal of ethylene oxide from a gaseous stream and in particular, relates to a system for removal of ethylene oxide from the stream effluent of an ethylene oxide sterilization unit.

The use of ethylene oxide as a gas sterilization medium is well known and has been widely employed for sterilizing reusable medical devices in small portable sterilizing units as well as in the manufacture of disposable, packaged, medical goods such as sutures, surgical sponges and the like which utilize large continuous or semicontinuous sterilizing chambers. In the case of small, portable sterilization units as well as for the large commercial units, a volume of ethylene oxide is introduced either alone or in combination with a diluent gas into a chamber containing the objects to be sterilized. The chamber is sealed and held in this condition until the sterilization process is completed. Thereafter, the ethylene oxide containing gas is discharged from the chamber and generally, the chamber is purged of residual gas.

Great care must be taken in disposing of the vented ethylene oxide containing gases as such gases are extremely toxic. Accordingly, in the case of small portable sterilizers, it has been suggested in U.S. Pat. No. 4,112,054 that the discharged gas from the sterilizer be charged into a vessel containing an aqueous acid solution. The vessel accepts the full discharge from the sterilizer and is sealed. The gas charged to the vessel dissolves into the liquid solution and, to a degree, reacts to form ethylene glycol and/or polyethylene glycol. After sufficient time has passed for the dissolution and reaction to take place, the liquid containing the dissolved ethylene oxide and reaction products is removed from the vessel and discharged in a sewer system. The now essentially ethylene oxide free carrier gases are vented from the vessel.

This batch operation works well for small portable sterilizing units provided that care is taken in controlling the temperature rise within the closed vessel after it has been charged with the discharge gases from the sterilizer. This temperature rise is a result of the exothermic reaction which takes place as the ethylene oxide is converted and dissolved and, since the system is closed, heat generated by the reaction acts to raise the temperature of the system. The adverse effect of this temperature rise is to shift the vapor-liquid equilibrium concentration of the ethylene oxide so as to cause a greater concentration of ethylene oxide in the vapor phase, i.e., the gases vented from the vessel. To counteract this tendency for rising temperatures, a large quantity of aqueous solution is provided in the vessel, as compared to the quantity of gas charged. This large quantity of liquid then acts as a heat sink to maintain the temperature rise within acceptable limits.

While the above-described batch-like system is said to be practical in connection with the use of small, portable, sterilization units, it is quite clear that such a system is totally impractical when applied to large commercial units. In the latter case, extremely large quantities of gas are to be vented from the sterilizer on a continuous or semicontinuous basis and if the aforementioned batch-like system were to be used, extremely large pressure vessels would be required. Moreover, an enormous quantity of aqueous acid solution would be required to preclude an impermissable temperature rise during the course of the exothermic reaction.

Accordingly, there is a need for a system for handling the vented ethylene oxide containing gas streams in a commercially practical manner.

SUMMARY OF THE INVENTION

In accordance with the teachings of this invention, a system is provided for removing and retaining ethylene oxide from a gaseous stream without the need for prohibitively large equipment or large quantities of liquid heat sink. Specifically, a method is provided for removing ethylene oxide from a gaseous stream in a continuous manner, unlike the batch-like system employed in the prior art. A vessel is provided containing an aqueous acid solution and having a gas diffusion means submerged in the solution. The gaseous stream from which the ethylene oxide is to be removed is continuously diffused through the gas diffusion means and bubbles up and out of the acid solution while the inert, essentialy ethylene oxide free gas, is continuously removed from above the solution. By continuously removing the inert ethylene oxide free gas, the problem of rising temperatures due to heat generated by the exothermic reaction is essentially obviated in that this heat is carried off as sensible heat in the inert gases. Accordingly, only a relatively small quantity of solution is required to maintain a relatively small temperature rise.

Because only a relatively small quantity of solution is employed, the residence time for the ethylene oxide to dissolve or react is greatly decreased. Accordingly, in accordance with the teachings of this invention, it is important to insure that the ethylene oxide containing gas entering the system be immediately diffused as soon as it contacts the acid solution. Diffusion means such as a plurality of manifolded, parallel, fritted glass cylinders are employed to insure such gas diffusion. It has been discovered that if the gaseous stream passes through diffusion means which create a pressure drop through such means of between 1 and 15 mm. of Hg, such pressure drop will correspond to sufficient gas diffusion to insure that at least about 95% of the ethylene oxide entering the system will be dissolved or reacted and retained by the solution. Preferably the pressure drop should be between 5 and 10 mm. of Hg.

The system of this invention allows for a relatively small quantity of aqueous acid solution to be used for purifying a large quantity of ethylene oxide containing gas. This is highly desirable in that in addition to reducing the size of the equipment for purification, a lesser quantity of the spent liquid must be discarded. Accordingly, it is preferred that no more than 100 ml of aqueous liquid per gram mole of ethylene oxide entering the system be employed in the system of the invention and more preferably no more than 60 ml/mole. This is in marked contrast to the batch-like systems of the prior art wherein at least 440 ml/mole of aqueous acid solution must be employed.

The relatively small quantities of liquid notwithstanding, it is still necesssary to dispose of such liquid and accordingly, for safety reasons, the liquid must first be neutralized, with for example, sodium hydroxide solution, before disposal. In this connection, it is desirable to have to handle as dilute an acid solution as is possible. On the other hand, the solution, in operation, must have a sufficient acidity to insure efficient removal of the ethylene oxide from the gaseous stream. It has been discovered that when the range of aqueous acid solution normality is about 0.35 to about 1.5 both these criteria can be satisfactorily met. Preferably, the aqueous acid solution normality should range from about 0.5 to about 1.25

DETAILED DESCRIPTION OF THE INVENTION

Figure 1:
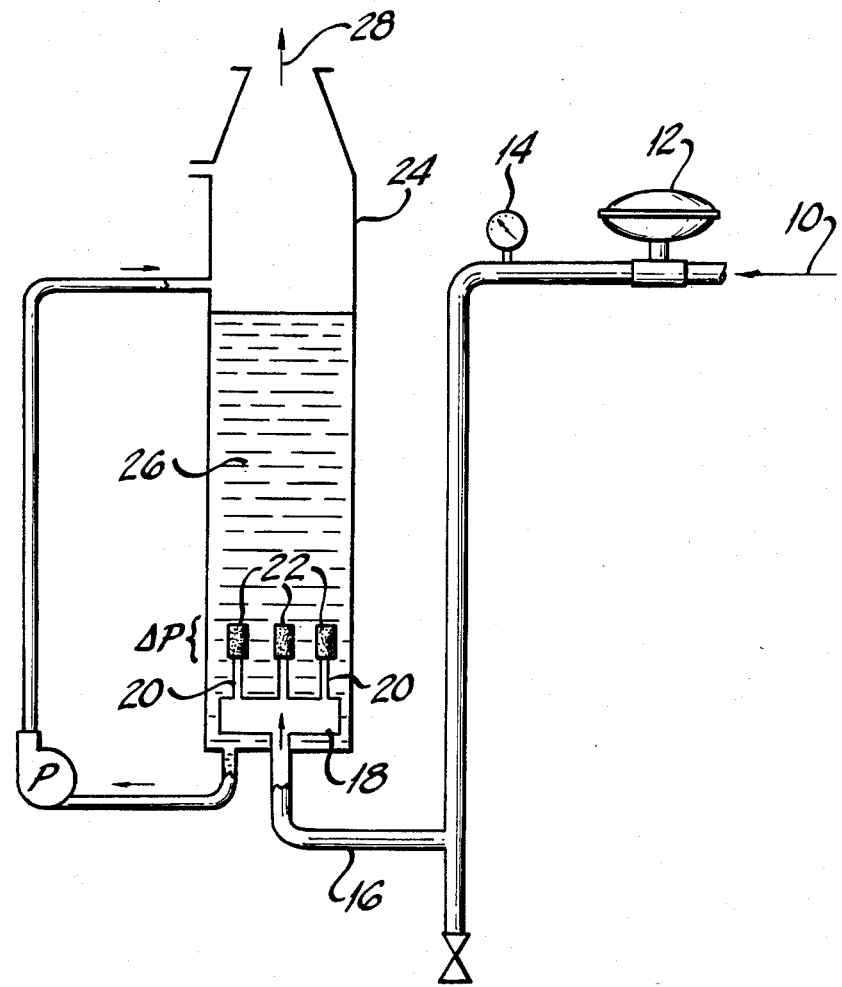
FIG. 1 is a schematic cross-sectional elevational view of the system of this invention.

Referring now to FIG. 1, shown there is a schematic, cross-sectional, elevational, view of the system of this invention for removing ethylene oxide from a gas stream. Such a stream, shown as stream 10, may be for example, the exhaust from a commercial sterilization unit and may comprise, in addition to ethylene oxide, inert gases such as nitrogen. Most commonly, commercial sterilization utilizes a mixture of ethylene oxide and carbon dioxide or a fluorinated hydrocarbon such as Freon. Generally the exhaust gas can contain from 10 to 90% by weight of ethylene oxide and more usually between 10 and 12% by weight. Most commercial sterilizers operate at above atmospheric pressures and so the exhaust gas, stream 10, is available to the system of this invention at pressures ranging from 20 to 50 pounds per square inch (absolute) and more usually at pressures of 20 to 40 p.s.i. Normally, the sterilizer exhaust gases are available to the system at temperatures of from 100° to about 165° F.

Stream 10 first flows through a pressure regulator 12 monitored by pressure gauge 14, wherein the pressure is throttled down to that necessary for the gas to flow through the system and be vented to the atmosphere. The stream of ethylene rich gas then flows through manifold piping 16 to manifold bladder 18 where it is distributed via a plurality or dispersion pipes 20 to a plurality of gas dispersion means 22. The manifold bladder 18, the dispersion pipes 20 and the gas dispersion means 22 all are located in vessel 24 and are submerged in aqueous acid solution 26 contained in vessel 24.

As the gas flows out of dispersion means 22 it is in the form of small bubbles which contact the aqueous acid solution and react therewith to form, among other reaction products, ethylene glycol. In the case, for example, of utilizing dilute sulfuric acid solution in vessel 24, the reaction is as follows:

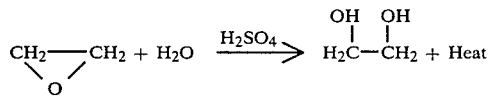

Alternatively, if hydrochloric acid is utilized, the reaction will be:

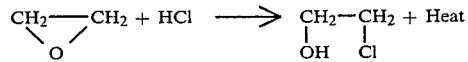

In any event, the ethylene glycol or chloroethylene glycol is extremely soluble and along with some dissolved, unreacted ethylene oxide, will be retained with the liquid solution while the essentially ethylene oxide free inert gas is vented to the atmosphere as stream 28.

Because stream 28 is continuously removed from the system as stream 10 as being charged to the system, a large part of the heat generated by the aforementioned reaction leaves in the form of sensible heat. Accordingly, very little volume of acid solution is required relative to a large inflow of ethylene oxide in stream 10. The aqueous acid solution utilized should be no more than 100 ml/gm mole of ethylene oxide charged to the unit before the liquid is disposed of and preferably no more than 60 ml/gm mole.

Without being bound by any theory, it is believed that the reaction converting ethylene oxide into ethylene glycol primarily takes place immediately at the point in the system where the gaseous stream first interfaces with the liquid; i.e., where the small gas bubbles leave the gas dispersion means. Thereafter, any unreacted ethylene oxide remains trapped and entrained within gas bubbles of primarily inert gas which bubbles grow as they expand and rise up through the liquid and vent to the atmosphere. Accordingly, to convert a preponderance of the ethylene oxide, it is important to insure that the gas is well dispersed when leaving the dispersing means. It has been discovered empirically, that when gas pressure drops across the dispersing means (ΔP in the drawing) is controlled to between 1 and 15 mm of Hg, good dispersion results and a highly efficient conversion of ethylene oxide is maintained. Preferably this pressure difference is controlled to between 5 and 10 mm of Hg.

While the choice of gas dispersing means is not critical provided that the gas is subdivided into small enough bubbles to accomplish the efficiencies required, one preferred form of dispersing means is the use of fritted glass cylinders. These cylinders, in flow communication with the gas dispersion pipes 20, comprise glass which has been treated to be microporous, i.e., to have channels which may be as small as one micron or less, through which the gas flows and exits from the surface of the cylinders as tiny bubbles. The number and dimension of these cylinders should be such as to lie within the pressure drop considerations specified herein and preferably to result in a nominal gas velocity of from 0.05 to about 0.20 per second. By the term "nominal gas velocity" it is meant the aggregate gas flow in cubic feet per second, divided by the aggregate external flow area of the fritted glass cylinders in square feet. For example, a total gas flow of 100 liters per minute at the surface of all of the fritted glass cylinders is equivalent to about 0.0648 cubic feet per second. If this gas flows from the surface of twenty two cylinders, each having a height of one inch and a diameter of 0.875, then the total aggregate external area is 86.89 square inches or 0.6034 square feet. Accordingly, nominal gas velocity will be 0.0648 cubic feet per second divided by 0.6034 square feet of flow area or 0.1074 ft./sec.

As has been described above, because the heat of reaction is to a large measure removed from the system as sensible heat in the continuously removed ethylene oxide free inert stream, there is no longer any need for large volumes of liquid in the system. However, it is important that liquid at a sufficient acidic concentration be provided to insure efficient conversion of the entering ethylene oxide. At the same time, too high an acid concentration will require extensive neutralization of the solution when it is discarded. It has been discovered that a balance between these considerations is reached when the aqueous acid solution is provided at a normality in the range of from about 0.35 to about 1.5. Preferably, the solution normality can range from about 0.5 to about 1.25.

EXAMPLE 1

A unit having the general configuration of that illustrated in FIG. 1 is in flow communication with a commercial, 100 cubic feet, ethylene oxide sterilizer. The vessel of the unit consists of a seven foot high column having an inside diameter of nine inches and is charged with 13.2 gallons of a 1.0 N aqueous sulfuric acid solution. The solution is at room temperature, approximately 21° C. Submerged at the bottom of the unit are 22 cylindrical fritted glass gas diffusers manifolded to be in parallel flow communication with the ethylene oxide rich exhaust gas stream from the sterilizer. Each of the fritted glass cylinders measures 1.0 inches in height and 0.875 inches in diameter.

In the preferred mode of operation, exhaust gas from the sterilizer is available at a pressure of 36.8 psig and consists of 12%, by weight, of ethylene oxide; the remainder being Freon 12 fluorinated hydrocarbon. The exhaust gas rate is 1 lb./min. or approximately 4 cubic feet/min., measured at 25° F. and one atmosphere pressure. The high pressure sterilizer exhaust gas is throttled through a pressure regulator to control the flow and maintain a pressure drop across each of the fritted glass cylinder of from 6 to 11 mm of Hg. Under these conditions the nominal gas velocity at the surface of the fritted tubes is controlled within the range of from 0.10 to 0.15 ft/sec. A sampling probe from a Perkin-Elmer Gas Chromatography Ethylene Oxide Continuous Monitor is positioned in the gas stream above the liquid level in the column to continuously monitor ethylene oxide content of the gases vented by the system. The vented gas is found to contain from 9 to 300 parts per million of ethylene oxide, corresponding to an efficiency (percent of ethylene oxide in sterilizer exhaust gas removed) of about 99.9%.

EXAMPLE 2

Figure 2:
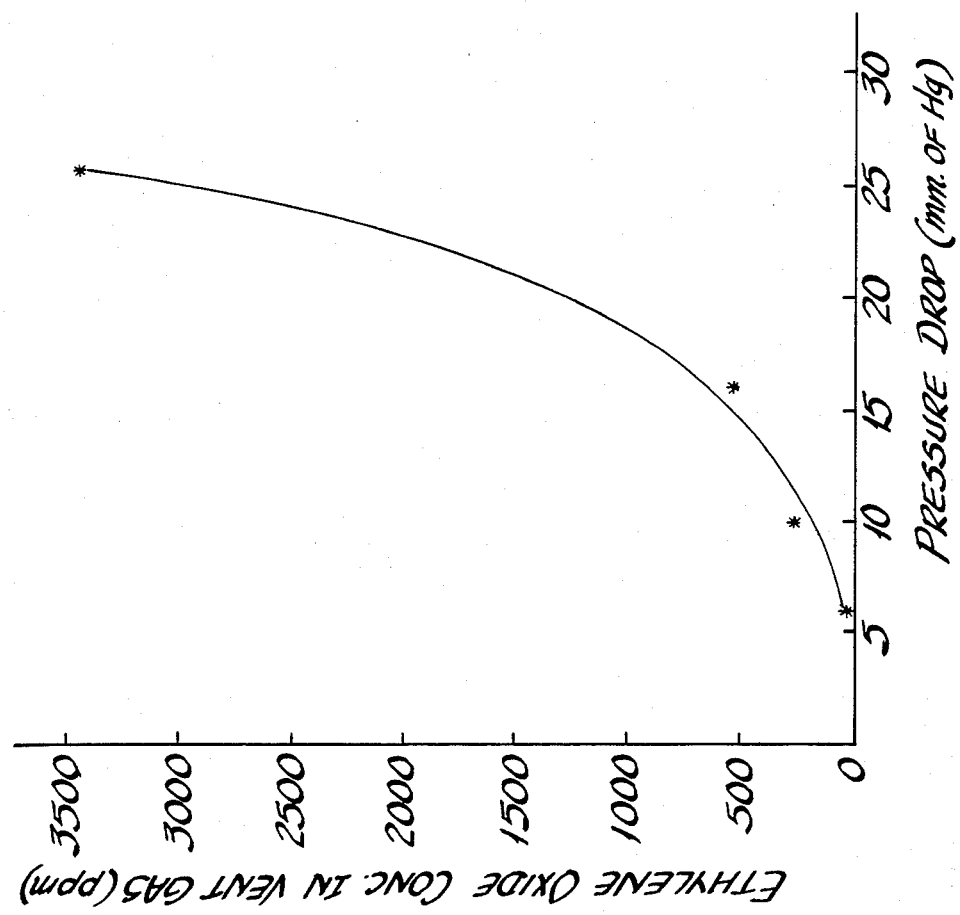
FIG. 2 is a graphical representation of the relationship between ethylene oxide gas content of the gas stream leaving the system of FIG. 1 as a function of the pressure drop across the gas diffusers.

A series of runs are performed as described in connection with the above example 1, with the exception that the pressure and flow downstream of the pressure regulator is varied to produce a varying pressure drop across the fritted glass cylinders. Table 1 below records the results in terms of ethylene oxide content in parts per million, in the vented gas a function of pressure drop, in mm. of Hg, across the fritted cylinders. FIG. 2 graphically depicts this relationship.

TABLE 1

| Pressure Drop (mm. of Hg) | Ethylene Oxide Conc. in Vent Gas ppm |
| --- | --- |
| 6 | 10 |
| 10 | 260 |
| 16 | 530 |

TABLE 1-continued

| Pressure Drop (mm. of Hg) | Ethylene Oxide Conc. in Vent Gas ppm |
| --- | --- |
| 26 | 3450 |

As can be seen from the above Table 1 and FIG. 2, as the pressure drop is maintained between 5 to 15 mm Hg, the vented gas is controlled to contain less than approximately 500 ppm ethylene. On the other hand, beyond a pressure drop of 15 mm of Hg, the ethylene oxide concentration of the vented gas increases rapidly with increasing pressure drop. It is clear therefor that controllable conditions will reside if the pressure drop is maintained below the knee in the curve, i.e., below 15 mm of Hg.

EXAMPLE 3

Figure 3:
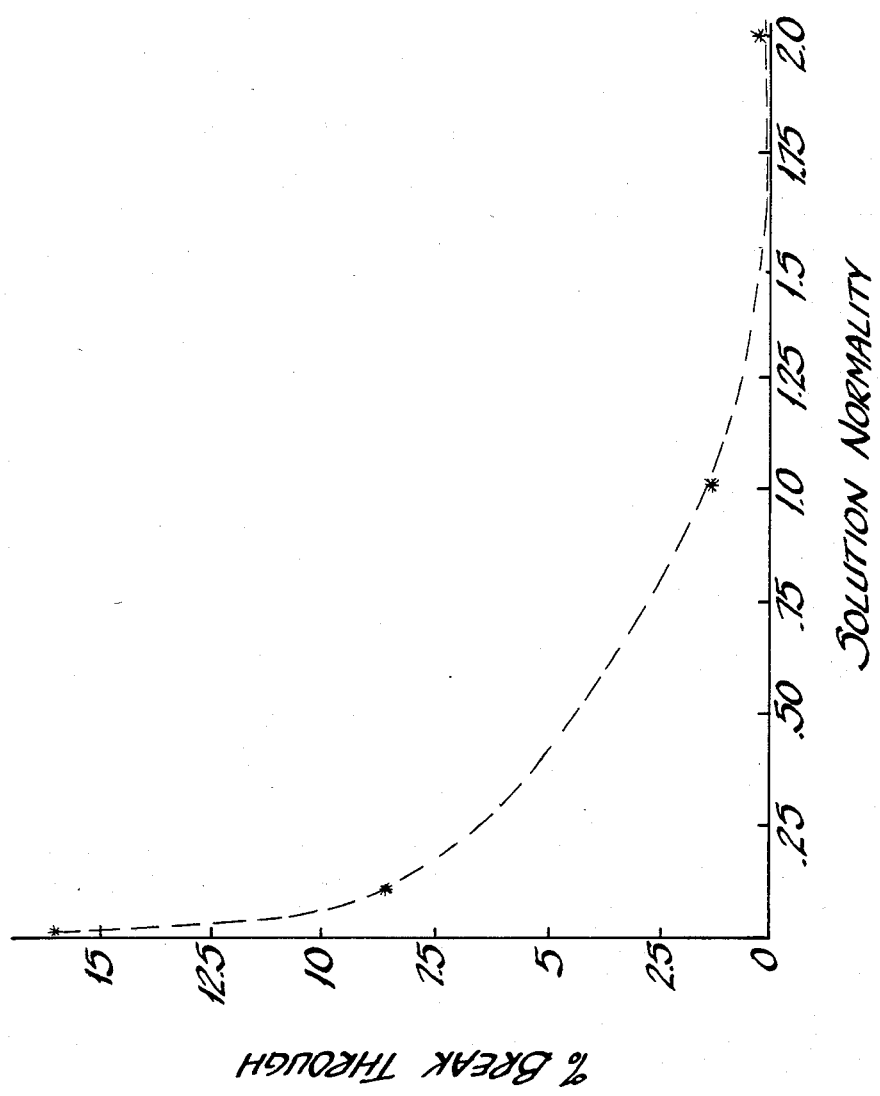
FIG. 3 is a graphical representation of the relationship between the breakthrough of the ethylene oxide front as a function of the normality of the aqueous acid solution.

To illustrate the effect of solution normality, a series of runs are made under the conditions of Example 1, with the exception that the normality of the solution is varied over a range of 0.01 to 2.0 N. The percentage, by weight, of ethylene oxide being vented after fourteen minutes of continuous operation and based on the inflow of ethylene oxide in the sterilizer exhaust gas is calculated and reported below in Table 2. These data are graphically illustrated in FIG. 3.

TABLE 2

| Solution Normality | % Break Through |
| --- | --- |
| 0.01 | 16.03 |
| 0.10 | 8.55 |
| 1.00 | 1.34 |
| 2.00 | <0.30 |

As can be seen from these data, a normality of at least 0.5 N insures at least a 95% efficiency for the first fourteen minutes of continuous operation. On the other hand little advantage is accrued from operating at a normality above 1.5.

What is claimed is:

1. A method for removing ethylene oxide from a gaseous stream comprising:
   providing a vessel containing an aqueous acid solution, said solution having a normality ranging from about 0.35 to about 1.5;
   providing said vessel with a gas diffusion means submerged in said solution;
   continuously introducing said gaseous stream into said acid solution by diffusing said gas through said gas diffusion means, the pressure drop of the gas across said gas diffusion means being controlled to between about 1 and about 15 millimeters of mercury;
   continuously withdrawing undissolved gas from the vessel;
   whereby said gas being diffused in said diffusion means to a degree sufficient to result in at least 95% of said ethylene oxide introduced into said vessel being retained in the aqueous solution.

2. The method of claim 1 wherein the pressure drop of the gas across said gas diffusion means ranges from about 5 to about 10 millimeters of mercury.

3. The method of claim 1 wherein the quantity of aqueous acid solution is no more than about 100 ml of solution per gram mole of ethylene oxide entering the vessel.

4. The method of claim 3 wherein the quantity of aqueous acid solution is no more than 60 ml of solution per gram mole of ethylene oxide entering the vessel.

5. The method of claim 1 wherein the normality of the aqueous acid solution ranges from about 0.35 to about 1.25.

6. The method of claim 1 wherein the nominal gas velocity ranges from about 0.05 to about 0.20 feet per second.

7. The method of claim 1 wherein said gas diffusion means comprising a plurality of fritted glass cylinders.

8. The method of claim 1 wherein the aqueous acid solution is a solution of sulfuric acid.

9. The method of claim 1 wherein said aqueous acid solution is a solution of hydrochloric acid.

* * * * *